ved Patent [19] [11] 4,017,616
Gomez et al. [45] Apr. 12, 1977

[54] PARENTERAL BENZODIAZEPINE COMPOSITIONS

[75] Inventors: Eloy A. Gomez, West Chester; Howard J. Levin, Norristown, both of Pa.

[73] Assignee: American Home Products Corporation, New York, N.Y.

[22] Filed: Apr. 13, 1973

[21] Appl. No.: 351,114

Related U.S. Application Data

[63] Continuation-in-part of Ser. No. 219,867, Jan. 21, 1972, abandoned.

[52] U.S. Cl. ............................................... 424/244
[51] Int. Cl.² ........................................ A61K 31/33
[58] Field of Search ................................... 424/244

[56] References Cited

UNITED STATES PATENTS 3,123,529  3/1964  Kariss et al. .................. 424/232 X
3,228,834  1/1966  Gans et al. .................... 424/244 X
3,296,249  1/1967  Bell ............................. 424/244 X

OTHER PUBLICATIONS

Merck Index, 8th ed., 1968, pp. 772–773.
Chemical Abstracts, 68:67592s, (1968).
Chemical Abstracts, 61:6224f, (1964).
Remington's Practice of Pharmacy, 13th ed., 1965, pp. 501 & 1132.

Primary Examiner—Leonard Schenkman
Attorney, Agent, or Firm—Robert Wiser

[57] ABSTRACT

Stable, non-aqueous parenteral dosage forms of benzodiazepine compounds comprise from about 10% to about 65% polyethylene glycol, from about 35% to about 90% propylene glycol, from 0% to about 10% benzyl alcohol, and 1 mg. to 15 mg. of benzodiazepine compound per ml.

6 Claims, No Drawings

PARENTERAL BENZODIAZEPINE COMPOSITIONS

CROSS-REFERENCE TO RELATED APPLICATION

This application is a continuation-in-part of U.S. application Ser. No. 219,867, filed Jan. 21, 1972, now abandoned.

BACKGROUND OF THE INVENTION

The 5-monocyclic aryl-1,3-dihydro-2H-1,4-benzodiazepin-2-one compounds which bear an oxygen containing substituent at position-3 of the benzodiazepine nucleus comprise an important class of medicinal agents which are useful, inter alia, as tranquilizers, anticonvulsants, and antianxiety agents. Typical of this class of compounds are 7-chloro-1,3-dihydro-3-hydroxy-5-phenyl-2H-1,4-benzodiazepine-2-one, also known as oxazepam, and 7-chloro-5-(o-chlorophenyl)-1,3-dihydro-3-hydroxy-2H-1,4-benzodiazepine-2-one, and very many others, as shown in U.S. Pat. No. 3,296,249. Although these compounds are orally active, a need exists for parental solutions of these drugs for use where oral adminstration is not feasible or desirable, such as in the case of an unconscious person, or one seriously disturbed, or where rapid onset of action is desired. Unfortunately, however, these 3-oxygenated 1,4-benzodiazepin-2-ones do not lend themselves to incorporation into the common parenteral formulations, e.g., aqueous solutions. The subject chemical compounds are themselves highly water insoluble. Further, they are so weakly basic that they do not form water soluble salts with pharmaceutically acceptable acids suitable for parenteral administration. As a result, the formulation of satisfactory parenteral preparations, which are physioligically acceptable, contain a sufficient concentration of drug to be medicinally useful, and possess sufficient chemical stability, has presented a continuing problem. U.S. Pat. Nos. 3,123,529 and 3,228,834 describe partially aqueous parenteral formulations for the benzodiazepine drugs diazepam and chlorodiazepoxide respectively (neither of which bears an oxygen containing substituent at position-3 of the benzodiazepine nucleus). Formulations of these types ae not suitable for the commercial preparation of parenteral solutions of the benzodiazepine compounds to which the present invention relates. A formula of the type described in U.S. Pat. No. 3,123,529 provides solutions of the subject benzodiazepines which are highly unstable; the 3,228,834 formula on the other hand describes a diluent which is mixed with the benzodiazepine compound only shortly before administration. The present invention, however, provides a non-aqueous parenteral solution which is highly stable on storage, may be administered directly, is physiologically acceptable, and contains medically useful amounts of drug.

SUMMARY OF THE INVENTION

The invention sought to be patented resides in the concept of a parenterally acceptable composition comprising from about 10% to about 65% polyethylene glycol, from about 35% to about 90% propylene glycol, from 0% to about 10% benzyl alcohol, and, per ml. of the above solution from about 1 mg. to about 15 mg. of benzodiazepine compound of the formula

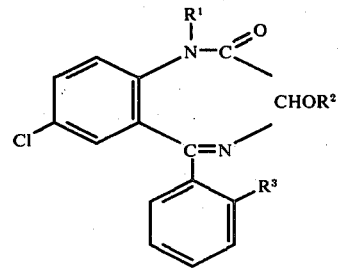

wherein $R^1$ and $R^2$ are independently hydrogen or methyl, and $R^3$ is hydrogen or chlorine.

The tangible embodiments of the invention are clear solutions suitable for parenteral injection. They are chemically quite stable on storage, and thus provide a dosage form which may be maintained in ready-to-use form, thus making unnecessary such undesirable operations as separate packaging of diluent and drug, or the need for reconstitution shortly before administration.

DESCRIPTION OF THE PREFERRED EMBODIMENTS

The formulations of the present invention may be readily prepared by simple admixing of the described constituents. Thus one simply mixes together the desired amounts of polyethylene glycol and propylene glycol within the scope of the invention, and adds thereto the required amount of the benzodiazepine compound, with stirring to achieve solution. If sterile materials are used, and sterile conditions are maintained, following filtration the resulting material is suitable for parenteral use with no further processing. Alternatively, the solution may be sterilized by procedures known in the art, such as bacteriological filtration. In either case, the solution is packaged under sterile conditions to provide a stable parenteral dosage form capable of undergoing storage for long periods of time with no significant deterioration.

The mixing of ingredients is conveniently performed at room temperature. Depending on the particular formulation and benzodiazepine compound used, however, it is sometimes desirable to dissolve the drug in the glycol mixture at slightly elevated temperature, as for example 55°-60°, to promote dissolution.

In preparing the formulations of the present invention, it is preferred to employ polyethylene glycol which is liquid at room temperature, for example, polyethylene glycol having an average molecular weight of 300 or 400; however, solid polyethylene glycols may also be employed.

Wherever percentages are given in the specification and in the claims, they represent percentages by volume and are based on the total volume of the solvent composition.

Although it is not essential to practice of the invention, in a preferred embodiment benzyl alcohol at a concentration of up to 10% may be incorporated in the composition. The benzyl alcohol has the desirable properties of exerting an anti-bacterial action and also of providing an anesthetic effect upon parenteral administration of the drug. Additionally, if desired, other substances such as bactericides may be added.

In addition to being useful for direct parenteral administration, the solutions of the invention are also compatible with physiological solutions such as water for injection, 5% dextrose in water, and physiological saline, and may be administered in admixture with such injection solutions.

The particular dosages of the compositions of the invention to be employed in therapy should be individualized, and will vary according to the particular condition being treated, the route of administration, the size and species of the animal being treated, and the particular benzodiazepine compound being administered. The determination of the particular dosage is well within the skill of the attending physician. Generally, a dosage which supplied from 1 to 75 mg. of drug is employed, and preferably from 5 to 50 mg., either intravenously or intramuscularly.

The following examples, which are not meant to be limitative, will further illustrate the practice of the invention.

EXAMPLE 1

18 ml. polyethylene glycol, molecular weight 300, is mixed with stirring with 75 ml. propylene glycol and 2 ml. benzyl alcohol. To this solution is added 1.5 g. of 7-chloro-5-(o-chlorophenyl)-1,3-dihydro-3-hydroxy-2H-1,4-benzodiazepine-2-one followed by the addition of sufficient propylene glycol to provide 100ml. solution. The mixture is stirred at room temperature to obtain a clear solution containing 15 mg./ml. drug.

Storage of the above solution at refrigerator temperature for 37 months showed satisfactory chemical and physical stability.

EXAMPLE II

In a similar manner to that of Example I, stable solutions containing 5 mg./ml. drug are prepared by substituting for the benzodiazepine compound of Example I. 0.5 g. of either 7-chloro-1,3-dihydro-3-hydroxy-5-phenyl-2H-1,4-benzodiazepin-2-one or 7-chloro-1,3-dihydro-3-hydroxy-1-methyl-5-phenyl-2H-1,4-benzodiazepin-2-one.

Example III 20 ml. polyethylene glycol, molecular weight 300 or 400, is admixed with 75 ml. propylene glycol. To this solution is added 1.0 g. of 7-chloro-5-(o-chlorophenyl)-1,3-dihydro-3-hydroxy-2H-1,4-benzodiazepin-2-one, with stirring, followed by the addition of sufficient propylene glycol to provide 100 ml. total volume, to yield a clear stable solution containing 10 mg. drug per ml.

Example IV 50 ml. polyethylene glycol, molecular weight 400, is mixed with 45 ml. propylene glycol. The glycol mixture is heated to 55° C., and there is added, with stirring, 0.5 g. of 7-chloro-5-(o-chlorophenyl)-1,3-dihydro-1-methyl-3-methoxy-2H-1,4-benzodiazepin-2one. A clear solution is obtained, which remains so upon cooling to room temperature or below. Sufficient propylene glycol is added to provide a total volume of 100 ml.

This solution, containing 5 mg. drug per ml. was stored for 24 months at room temperature with no losses being observed.

The subject matter which the applicants regard as their invention is particularly pointed out and distinctly claimed as follows:

1. A parenterally acceptable composition comprising from about 10% to about 65% polyethylene glycol, from about 35% to about 90% propylene glycol, from 0% to about 10% benzyl alcohol, and, per ml. of the above solution, from about 1 mg. to about 15 mg. of a benzodiazepine compound of the formula:

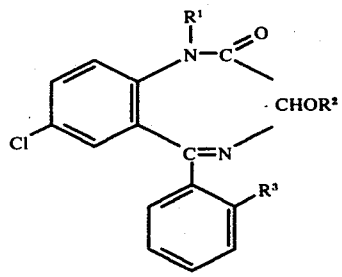

wherein $R^1$ and $R^2$ are independently hydrogen or methyl, and $R^3$ is hydrogen or chlorine, said composition being substantially free of water.

2. A composition according to claim 1 wherein $R^1$ and $R^2$ are hydrogen, and $R^3$ is chlorine.

3. A composition according to claim 1 wherein $R^1$ is methyl, $R^2$ is methyl, and $R^3$ is chlorine.

4. A composition according to claim 2 wherein the polyethylene glycol concentration is about 18%, the propylene glycol concentration is about 80%, and the benzyl alcohol concentration is about 2%.

5. A composition according to claim 2 wherein the polyethylene glycol concentration is about 20%, and the propylene glycol concentration is about 80%.

6. A composition according to claim 3 wherein the polyethylene glycol concentration is about 50% and the propylene glycol concentration is about 50%.

* * * * *